(12) United States Patent
Gerst et al.

(10) Patent No.: US 9,773,060 B2
(45) Date of Patent: Sep. 26, 2017

(54) SYSTEM AND METHOD FOR PROVIDING AUTOMATIC SETUP OF A REMOTE PATIENT CARE ENVIRONMENT

(75) Inventors: Kimberly S. Gerst, Eden Prairie, MN (US); Benjamin L. Somberg, Shoreview, MN (US); Bharat K. Jain, Eden Prairie, MN (US); Larry D. Canady, Ham Lake, MN (US)

(73) Assignee: Cardiac Pacemaker, Inc., St. Paul, MN (US)

( * ) Notice: Subject to any disclaimer, the term of this patent is extended or adjusted under 35 U.S.C. 154(b) by 2635 days.

(21) Appl. No.: 11/516,300

(22) Filed: Sep. 5, 2006

(65) Prior Publication Data

US 2008/0059239 A1  Mar. 6, 2008

(51) Int. Cl.

| | |
|---|---|
| G06F 19/10 | (2011.01) |
| G06F 17/30 | (2006.01) |
| A61B 5/00 | (2006.01) |
| G06F 19/00 | (2011.01) |
| G06Q 50/24 | (2012.01) |
| H04W 12/06 | (2009.01) |
| H04L 29/08 | (2006.01) |
| H04L 29/14 | (2006.01) |
| H04W 84/18 | (2009.01) |

(52) U.S. Cl.
CPC ...... *G06F 17/30861* (2013.01); *A61B 5/0002* (2013.01); *G06F 19/3418* (2013.01); *G06Q 50/24* (2013.01); *H04L 67/04* (2013.01); *H04L 69/40* (2013.01); *H04W 12/06* (2013.01); *H04W 84/18* (2013.01)

(58) Field of Classification Search
USPC ........................................................ 705/2–4
See application file for complete search history.

(56) References Cited

U.S. PATENT DOCUMENTS

| | | |
|---|---|---|
| 5,603,331 A | 2/1997 | Heemels et al. |
| 5,652,570 A | 7/1997 | Lepkofker |

(Continued)

FOREIGN PATENT DOCUMENTS

| | | |
|---|---|---|
| JP | 2002366653 | 12/2002 |
| WO | WO 00/62664 | 10/2000 |

(Continued)

OTHER PUBLICATIONS

Health Insurance Portability and Accountability Act of 1996, Pub. L. No. 104-191, 110 Stat. 1936 (1996).

(Continued)

*Primary Examiner* — Mark Holcomb
(74) *Attorney, Agent, or Firm* — Pauly, DeVries Smith & Deffner LLC (57) ABSTRACT

A system and method for providing automatic setup of a remote patient care environment. Connectivity to a centralized server over a network connection is confirmed. Data reporting for a patient by one or more monitoring devices that are wirelessly connectable is induced through control provided through a user interface. Each of the devices is registered as the device attempts to establish a wireless connection and report the data conditioned on permission for access. Upon granting of the permission for access, the device is wirelessly connected and the data is subsequently received over the wireless connection.

31 Claims, 6 Drawing Sheets

(56) References Cited

U.S. PATENT DOCUMENTS

| | | | |
|---|---|---|---|
| 5,687,734 | A | 11/1997 | Dempsey et al. |
| 5,716,382 | A * | 2/1998 | Snell ............................ 607/30 |
| 5,919,141 | A | 7/1999 | Money et al. |
| 6,014,432 | A | 1/2000 | Modney |
| 6,024,699 | A | 2/2000 | Surwit et al. |
| 6,083,248 | A | 7/2000 | Thompson |
| 6,168,563 | B1 | 1/2001 | Brown |
| 6,171,256 | B1 | 1/2001 | Joo et al. |
| 6,263,245 | B1 * | 7/2001 | Snell ............................ 607/60 |
| 6,290,646 | B1 | 9/2001 | Cosentino et al. |
| 6,416,471 | B1 * | 7/2002 | Kumar et al. ............... 600/300 |
| 6,454,705 | B1 | 9/2002 | Cosentino et al. |
| 6,827,670 | B1 | 12/2004 | Stark et al. |
| 6,878,112 | B2 * | 4/2005 | Linberg et al. ............. 600/300 |
| 6,882,883 | B2 * | 4/2005 | Condie et al. .................. 607/11 |
| 6,893,396 | B2 * | 5/2005 | Schulze et al. ............. 600/300 |
| 7,027,872 | B2 | 4/2006 | Thompson |
| 7,545,528 | B2 | 6/2009 | Takabayashi et al. |
| 7,801,596 | B2 * | 9/2010 | Fischell et al. ............. 600/523 |
| 7,859,400 | B2 * | 12/2010 | Urbaszek et al. ....... 340/539.12 |
| 2001/0051787 | A1 * | 12/2001 | Haller et al. ................... 604/66 |
| 2002/0013538 | A1 * | 1/2002 | Teller ............................ 600/549 |
| 2004/0102998 | A1 | 5/2004 | Bao et al. |
| 2004/0103001 | A1 | 5/2004 | Mazar et al. |
| 2006/0253300 | A1 | 11/2006 | Somberg et al. |
| 2007/0156626 | A1 * | 7/2007 | Roehm et al. ................ 706/924 |
| 2010/0063840 | A1 | 3/2010 | Hoyme et al. |
| 2010/0210920 | A1 * | 8/2010 | Ziv et al. ..................... 600/301 |

FOREIGN PATENT DOCUMENTS

| | | |
|---|---|---|
| WO | WO-2004060043 | 7/2004 |
| WO | WO-2005091205 | 9/2005 |
| WO | WO-2005091546 | 9/2005 |
| WO | WO-2006051464 | 5/2006 |

OTHER PUBLICATIONS

E. Hammond, "National Committee on Vital and Health Statistics, Subcommittee on Health Data Needs, Standards and Security," http://www.ncvhs.hhs.gov/970211t3.htm, pp. 1-4 (Feb. 11, 1997).

Security and Electronics Signature Standards, 63 Fed. Reg. 155 (proposed Aug. 12, 1998).

Response to European Communication filed Feb. 8, 2010, in European Application No. 07837777.7, corresponding to U.S. Appl. No. 11/516,300, 4 pages.

"European Examination Report, Communication pursuant to Article 94(3) EPC. from the European Patent Office in EP Patent Application No. 07837777.7", corresponding to U.S. Appl. No. 11/516,300, Jul. 31, 2009, 4 pages.

"PCT Notification Concerning Transmittal of International Preliminary Report on Patentability and Written Opinion of the International Searching Authority for International Application No. PCT/US2007/019405", corresponding to U.S. Appl. No. 11/516,300, mailed Apr. 14, 2008, 7 pages.

"First Office Action", from JP Application No. 2009526764, mailed Sep. 13, 2012, (pp. 1-5) Including English translation.

Translated Abstract and Drawings for JP-2002051991, Published Feb. 19, 2002, Toshihiko, Yasui et al (5 pages).

Translated Abstract and Drawings for JP-2000132622, Published May 12, 2000 Yoshida, Keiichi et al (5 pages).

Translated Abstract and Drawings for Translated Abstract for JP-2005346533, Published Dec. 15, 2005, Saito, Junichi et al (2 pages).

Translation of "Notice of Reasons for Rejection", for Japan Application No. 2009-526764, mailed Mar. 6, 2013 (7 pages).

* cited by examiner

SYSTEM AND METHOD FOR PROVIDING AUTOMATIC SETUP OF A REMOTE PATIENT CARE ENVIRONMENT

FIELD OF THE INVENTION

The invention relates in general to remote patient care and, specifically, to a system and method for providing automatic setup of a remote patient care environment.

BACKGROUND OF THE INVENTION

Remote patient management enables a clinician, such as a physician, nurse, or other healthcare provider, to follow patient well-being through homecare medical devices that can collect and forward patient data without requiring the presence or assistance of medical personnel. Remote patient management can be provided over a data communications network, such as the Internet. One or more medical devices per patient are remotely interconnected with a centralized server via dedicated patient management devices, such as repeaters, installed in patients' homes. The patient management devices supplement traditional programmers that interrogate patient medical devices in-clinic. This infrastructure allows patient well-being to be continually monitored and centrally analyzed by professional healthcare staff without the costs of office visits.

Patient physiometry can be measured and recorded through dedicated sensors or sensors incorporated into a medical therapy device, such as a pacemaker or defibrillator. The recorded patient physiometry is periodically uploaded to dedicated patient management devices for local analysis and relay to the centralized server. Thus, to effect remote patient management, each patient management device must be able to interface remotely to the centralized server and locally to the sensors and patient therapy devices.

Ensuring the operability of remote and local interfaces is a prerequisite to providing remote patient care. Existing remote care environment setup requires manual configuration and testing of each component and places the onus on the patient to ensure satisfactory operation. Pragmatically, individual patients, particularly those who are aged, infirm, or handicapped, are not necessarily technically savvy and could be challenged if required to manually set up a remote management environment. Nevertheless, a caregiver must still ensure that each patient management device can connect to both the centralized server and to each of the sensors and patient therapy devices before beginning remote care and establishing service. The caregiver must also address anomalies occurring during setup. However, to minimize time, cost, and resources expended, only those anomalies that result in a complete failure of operation should be escalated.

Setup is only the first step in providing remote care. The configurations and settings of the devices can change over time. Existing devices may be removed or replaced and new devices may be added. The operational parameters or firmware might respectively require reprogramming or patching. Each change potentially entails redoing the setup and requiring a patient to manually swap out devices can be expensive, time-consuming, and impracticable.

Following successful setup, the patient, or attendant, where applicable, must to be trained on the proper operation of the patient management device and patient-operable sensors and medical therapy devices. Effective training, as well as testing, requires instruction and practice, but using live data can needlessly consume resources or affect patient well being if incorrectly performed.

Therefore, there is a need for facilitating transparent and automated setup of a remote patient care environment for patients that can support both initial and subsequent installation and configuration of sensors, patient therapy devices, and patient management devices.

SUMMARY OF THE INVENTION

A remote patient care environment is setup through an automated sequence of operations that commence upon the initial power up of a patient management device or at the initiative of a patient or remote source, such as a centralized server or clients. A connection to the centralized server is first established to both confirm that the server connection is operable and to receive the most up-to-date configurations and profiles. The patient management device thereafter awaits requests to upload patient data from one or more locally-situated medical devices, such as dedicated sensors and medical therapy devices. Data reporting is induced to both bootstrap and initialize connections from each medical device and to help train the patient or attendant in the operation of the patient management device and medical devices. As each medical device attempts patient data upload, the patient medical device establishes a secure connection and, as necessary, reconfigures the sending medical device. Thereafter, remote patient management can begin.

One embodiment provides a system and method for providing automatic setup of a remote patient care environment. Connectivity to a centralized server over a network connection is confirmed. Data reporting for a patient by one or more monitoring devices that are wirelessly connectable is induced through control provided through a user interface. Each of the devices is registered as the device attempts to establish a wireless connection and report the data conditioned on permission for access. Upon granting of the permission for access, the device is wirelessly connected and the data is subsequently received over the wireless connection.

Still other embodiments will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Automated Patient Management Environment

Figure 1:
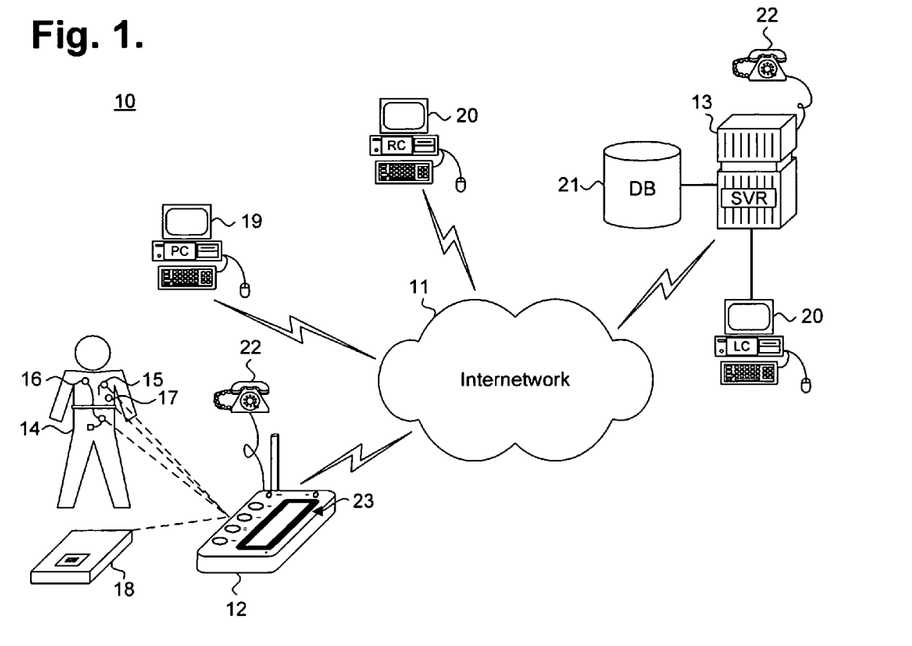
FIG. 1 is a functional block diagram showing, by way of example, an automated patient management environment.

Automated patient management encompasses a range of activities, including remote patient management and automatic diagnosis of patient health, such as described in commonly-assigned U.S. Patent application Pub. No. US2004/0103001, published May 27, 2004, pending, the disclosure of which is incorporated by reference. Such activities can be performed proximal to a patient, such as in the patient's home or office, centrally through a centralized server, such from a hospital, clinic or physician's office, or through a remote workstation, such as a secure wireless mobile computing device. FIG. 1 is a functional block diagram showing, by way of example, an automated patient management environment 10. In one embodiment, a patient 14 is proximal to one or more patient monitoring or communications devices, such as a patient management device 12, which are interconnected remotely to a centralized server 13 over an internetwork 11, such as the Internet, or through a public telephone exchange 22, such as a conventional or mobile telephone network. Other patient monitoring or communications devices are possible. In addition, the internetwork 11 can provide both conventional wired and wireless interconnectivity. In one embodiment, the internetwork 11 is based on the Transmission Control Protocol/Internet Protocol (TCP/IP) network communication specification, although other types or combination of networking implementations are possible. Similarly, other network topologies and arrangements are possible.

Each patient management device 12 includes a user interface 23 and is uniquely assigned to a patient under treatment 14 to provide a localized and network-accessible interface to one or more medical devices 15-18, either through direct means, such as wired connectivity, or through indirect means, such as induction or selective radio frequency or wireless telemetry based on, for example, "strong" Bluetooth or IEEE 802.11 wireless fidelity "WiFi" and "WiMax" interfacing standards. Other configurations and combinations of patient data source interfacing are possible.

The medical devices 15-18 collect and forward the patient data 22 either as a primary or supplemental function. Patient data includes physiological measures, which can be quantitative or qualitative, parametric data regarding the status and operational characteristics of the patient data source itself, and environmental parameters, such as the temperature or time of day. Other types of patient data are possible.

The medical devices 15-18 include, by way of example, medical therapy devices that deliver or provide therapy to the patient 14, medical sensors that sense patient physiometry, and measurement devices for collecting environmental and other data occurring independent of the patient 14. Each medical device 15-18 can generate one or more types of patient data and can incorporate one or more components for delivering therapy, sensing physiological data, measuring environmental parameters, or a combination of functionality. Medical therapy devices include implantable medical devices (IMDs) 15, such as pacemakers, implantable cardiac defibrillators (ICDs), drug pumps, and neuro-stimulators, and external medical devices (EMDs) 16. Medical sensors include implantable sensors 17, such as implantable heart and respiratory monitors and implantable diagnostic multi-sensor non-therapeutic devices, and external sensors 18, such as thermometers, heart rate monitors, Holter monitors, spirometers, weight scales, and blood pressure cuffs. External medical devices and sensors can operate autonomously or under patient, attendant, or caregiver control; and can include a user interface for receiving or providing subjective feedback or communications.

Prior to commencing remote patient care, the environment 10 must be setup to ensure that the patient management device 12 is usable by the patient and can reliably communicate with both locally-situated medical devices 15-18 and the remotely-located centralized server 13. Additionally, any changes to the configurations of the patient management device 12 or medical devices 15-18 should be addressed to avoid further unnecessary interruptions or delays in starting remote care. Accordingly, on initial power up or at the initiative of a patient 14 or other source, such as the centralized server 13 or clients 20, the patient management device 12 executes an automated setup procedure that sets up and tests each device connection and applies any changes to device configurations, as further described below beginning with reference to FIG. 3. Following successful setup, patient data 22 is collected by the medical devices 15-18 for forwarding to a patient management device 12, which can analyze and, in turn, also forward the patient data 22 to the centralized server 13.

In a further embodiment, data values can be directly entered by a patient 14. For example, answers to health questions could be input into a patient system 19, such as a personal computer with user interfacing means, such as a keyboard, display, microphone, and speaker. Such patient-provided data values could also be collected as patient information. In one embodiment, the medical devices 15-18 collect the quantitative objective physiological measures on a substantially continuous or scheduled basis and also record the occurrence of events, such as therapy or irregular readings. In a further embodiment, the patient management device 12, patient system 19, or similar device record or communicate qualitative subjective quality of life (QOL) measures that reflect the personal impression of physical well-being perceived by the patient 14 at a particular time. Other types of patient data collection, periodicity and storage are possible.

In a further embodiment, the collected patient data can also be accessed and analyzed by one or more clients 20, either locally-configured or remotely-interconnected over the internetwork 11. The clients 20 can be used, for example, by clinicians to securely access stored patient data 22 assembled in a database 21 and to select and prioritize patients for health care provisioning, such as respectively described in commonly-assigned U.S. patent application Ser. No. 11/121,593, filed May 3, 2005, pending, and U.S. patent application Ser. No. 11/121,594, filed May 3, 2005, pending, the disclosures of which are incorporated by reference. Although described herein with reference to physicians or clinicians, the entire discussion applies equally to organizations, including hospitals, clinics, and laboratories, and other individuals or interests, such as researchers, scientists, universities, and governmental agencies, seeking access to the patient data.

In a further embodiment, patient data 22 is safeguarded against unauthorized disclosure to third parties, including during collection, assembly, evaluation, transmission, and storage, to protect patient privacy and comply with recently enacted medical information privacy laws, such as the Health Insurance Portability and Accountability Act (HIPAA) and the European Privacy Directive. At a minimum, patient health information that identifies a particular individual with health- and medical-related information is treated as protectable, although other types of sensitive information in addition to or in lieu of specific patient health information could also be protectable.

Preferably, the server 13 is a server-grade computing platform configured as a uni-, multi- or distributed processing system, and the patient systems 19 and clients 20 are general-purpose computing workstations, such as a personal desktop or notebook computer. In addition, the patient management device 12, server 13, patient systems 19, and clients 20 are programmable computing devices that respectively execute software programs and include components conventionally found in computing device, such as, for example, a central processing unit (CPU), memory, network interface, persistent storage, and various components for interconnecting these components.

Task Hierarchy

Figure 2:
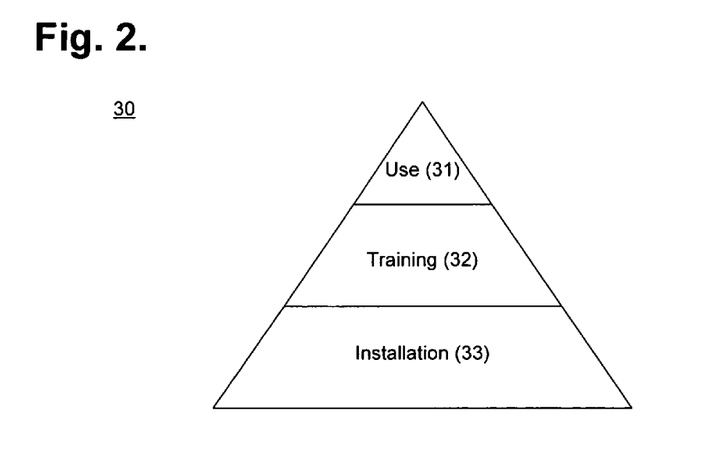
FIG. 2 is a block flow diagram showing, by way of example, a hierarchy of tasks to be performed in a remote patient care environment.

From a usability perspective, setup and data reporting involve distinct yet related sets of tasks. FIG. 2 is a block flow diagram showing, by way of example, a hierarchy of tasks 30 to be performed in a remote patient care environment 10. The tasks 30 can be grouped into installation 33, training 32, and use 31. Installation 33 is potentially the most-involved set of tasks, which includes configuring the patient medical device 12 and possibly one or more of the medical devices 15-18. The wide range of device types and configurations implies a host of physical device combinations and operational characteristic settings. Installation 33 further includes ensuring that the connection to the centralized server 13 and to each of the medical devices 15-18 is properly configured and operable. Other installation-related tasks are possible.

To a lesser degree, training 32 includes those tasks necessary to enable a patient or attendant to both gain familiarity with and be able to preferably perform limited troubleshooting of the patient management device 12 and those medical devices 15-18 with patient-operable features. Training 32 can include learning to navigate device menus and options, operating device controls, and properly obtaining patient data measurements, such as positioning a blood pressure cuff to take a correct reading. Other training-related tasks are possible.

Finally, use 31 simply entails the day-to-day measuring, recording, analysis, and relay of patient data between the medical devices 15-18, patient management device 12, and centralized server 13. Tasks falling within use 31 can overlap with those previously performed during training 32 and installation 33. Other use-related tasks are possible.

Automated Setup

Figure 3:
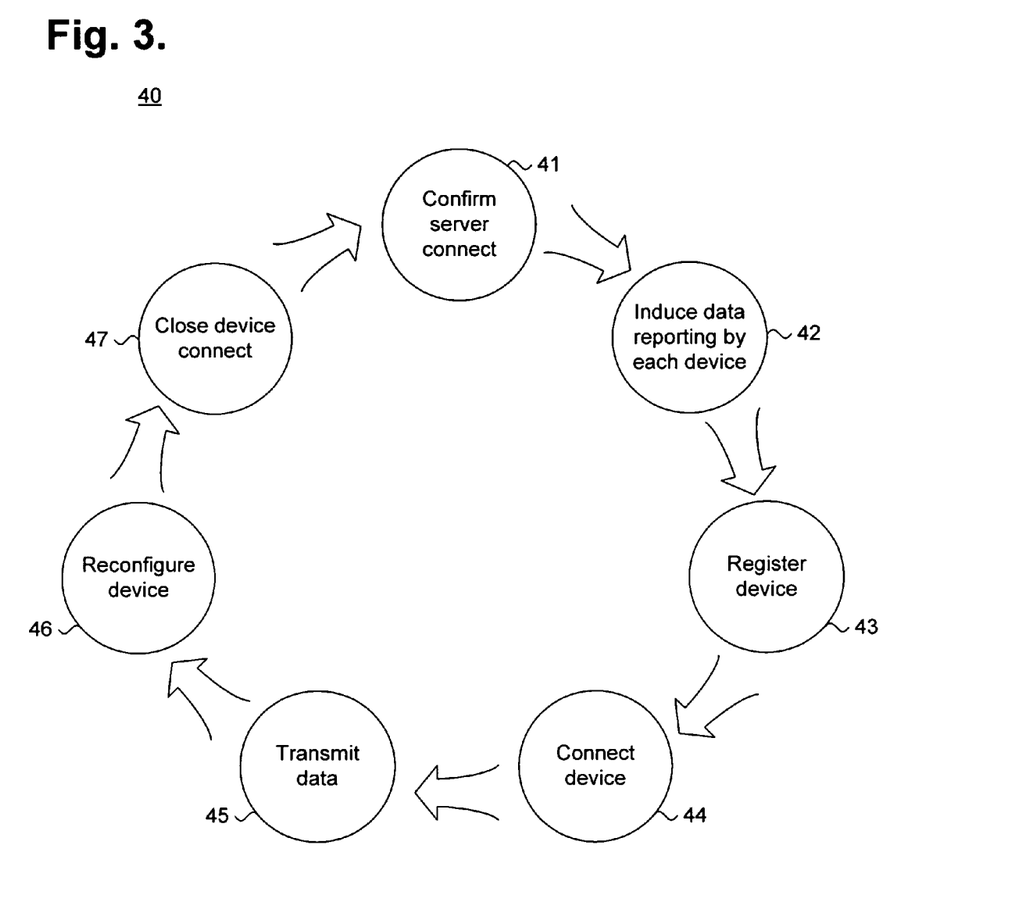
FIG. 3 is a process flow diagram showing automated setup of the remote patient care environment of FIG. 1, in accordance with one embodiment.

The tasks performed during training 32 and installation 33 can be automated. FIG. 3 is a process flow diagram showing automated setup 40 of the remote patient care environment 10 of FIG. 1, in accordance with one embodiment. During automated setup 40, the patient management device-to-centralized server connection and individual medical device-to-patient management device connections are automatically established and, where applicable, devices are reconfigured.

Initially, the connection to the centralized server 13 is confirmed (operation 41) upon the initial power up of a patient management device 12 or at the initiative of the patient 14 or other source, such as the centralized server 13 or clients 20. The patient 14 might need to reconfirm that all components remained working together if the patient management device 12 has been moved to a new location. Similarly, the centralized server 13 might need to revise the environment 10 based on knowledge of changes applicable to the environment 10, such as the addition of a new sensor. Other sources that trigger automated setup 40 are possible.

For a network-based server connection, the patient management device 12 attempts to establish a secure on-line connection with the centralized server 13 over a wired or wireless interface via the internetwork 11. For a telephone-based server connection, the patient management device 12 attempts to establish a dial-up connection to the centralized server 13 over a POTS (Plain Old Telephone System) or cellular connection. Other types of server connections are possible. Once the centralized server connection is established, the patient management device 12 retrieves configurations and profiles, as further described below with reference to FIG. 5.

Figure 6:
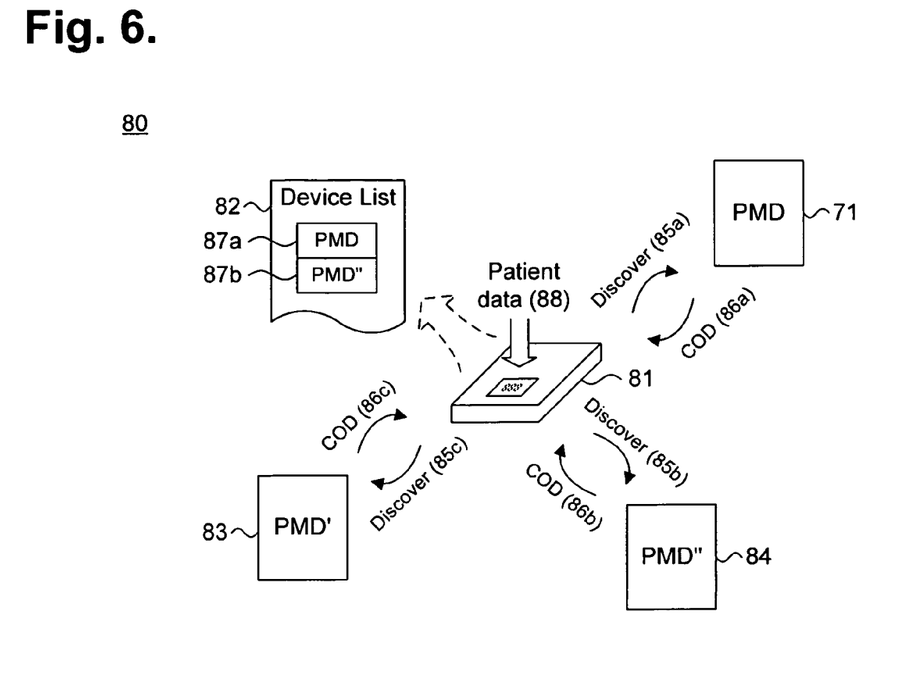
FIG. 6 is a process flow diagram showing device registration in the remote patient care environment of FIG. 1.

Next, the patient management device 12 induces data reporting by each device (operation 42), as further described below with reference to FIG. 6. "Inducing" data reporting can include requiring the patient to perform a particular action that enables the medical device 15-18 to take a data measurement, such as stepping on a weight scale or triggering a patient-initiated interrogation of an implantable medical device. Other induced data reporting actions can occur automatically without patient participation or cooperation.

The induced data reporting provides each medical device 15-18 with a starting point for establishing an initial connection with the patient management device 12. Each patient management device 12 is uniquely assigned to an individual patient 14, yet several eligible medical devices 15-18 may fall within the operational range of the patient medical device 12. Accordingly, each device must first register with the patient management device 12 (operation 43), which will only allow the device to subsequently connect and transmit data (operation 44 and 45, respectively) if the device has the proper permissions for access, as further described below with reference to FIGS. 7 and 8.

Figure 9:
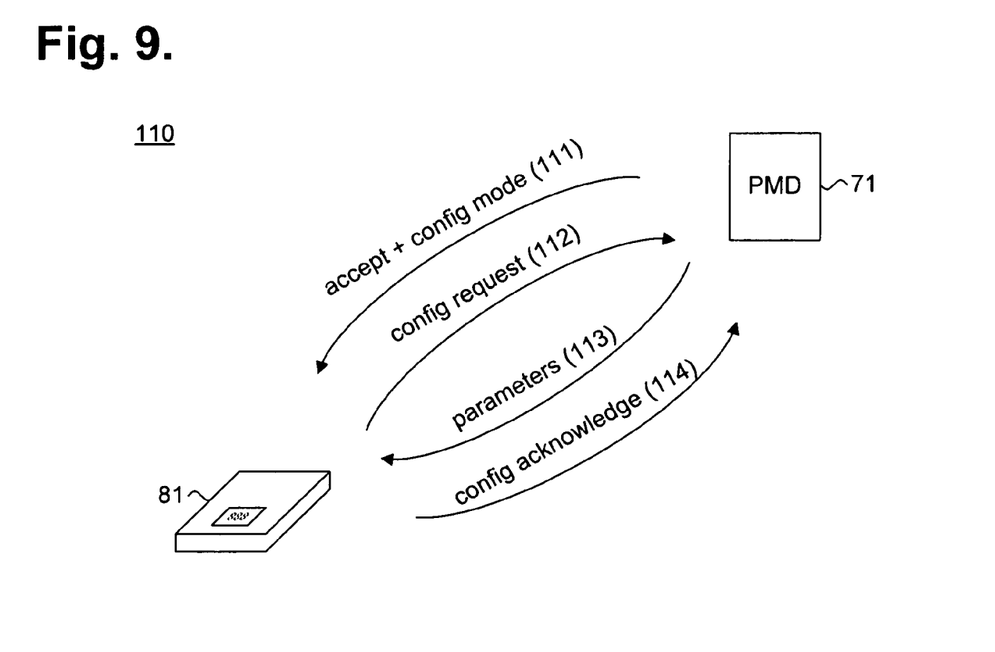
FIG. 9 is a process flow diagram showing data transmission and device reconfiguration in the remote patient care environment of FIG. 1.

Additionally, each medical device 15-18, as well as the patient management device 12, can be reconfigured (operation 46) as part of the automated setup process, as further described below with reference to FIG. 9. Lastly, each device connection is closed (operation 47). The patient management device 12 can also confirm successful setup to the centralized server 13 to signal readiness to the caregiver for beginning remote patient care. Other automated setup tasks are possible.

Data Reporting

Figure 4:
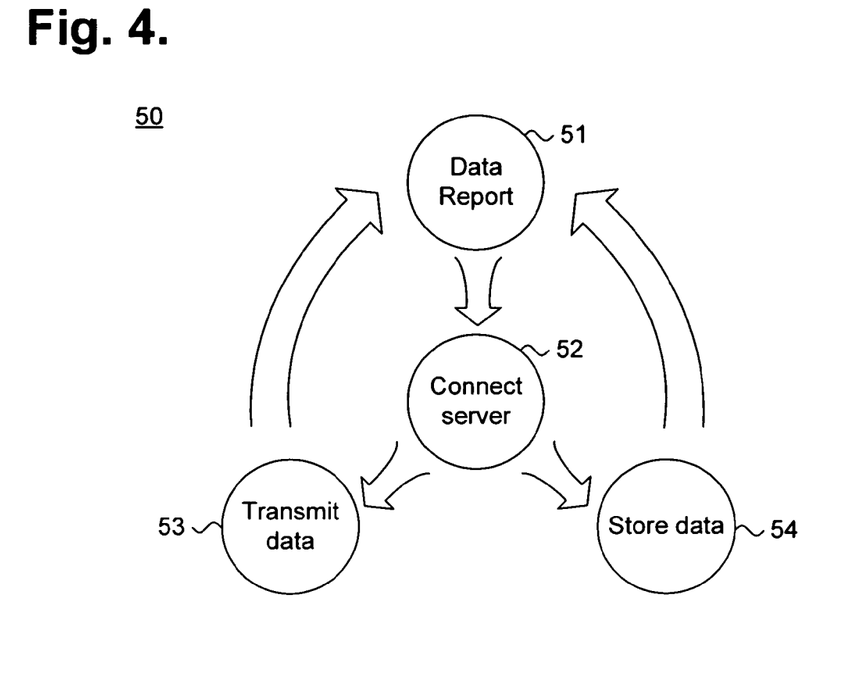
FIG. 4 is a process flow diagram showing data reporting in the remote patient care environment of FIG. 1.

Each patient management device 12 periodically receives patient data from the medical devices 15-18, which can be optionally analyzed prior to being relayed to the centralized server 13. FIG. 4 is a process flow diagram showing data reporting 50 in the remote patient care environment 10 of FIG. 1. Generally, to minimize the processing, storage, and power consumption overhead imposed on each medical device 15-18, patient data is only reported (operation 51) at the initiative of the reporting patient medical device 15-18, as a form of data push. Alternatively, the patient management device 12 could periodically poll one or more of the medical devices 15-18 to request stored patient data, as a form of data pull. Other forms of data reporting are possible.

The patient data that has been reported to a patient management device 12 can be either asynchronously reported to the centralized server 13 as received from each medical device 15-18, or can be periodically relayed in a batch to minimize network resource consumption. Upon successful receipt of patient data, the patient management device 12 attempts to connect to the centralized server 13 (operation 52) using the server connection previously established during automated setup. If successful in establishing a connection, the patient management device 12 transmits the patient data (operation 53) and returns to awaiting further patient data reports (operation 51). Otherwise, if unsuccessful in connecting, the patient management device 12 stores the patient data (operation 51) and returns to awaiting further patient data reports (operation 51). The patient management device 12 reattempts transmission of the stored patient data during the next reporting cycle. Other forms of data reporting are possible.

Detailed Setup Operations

Figure 5:
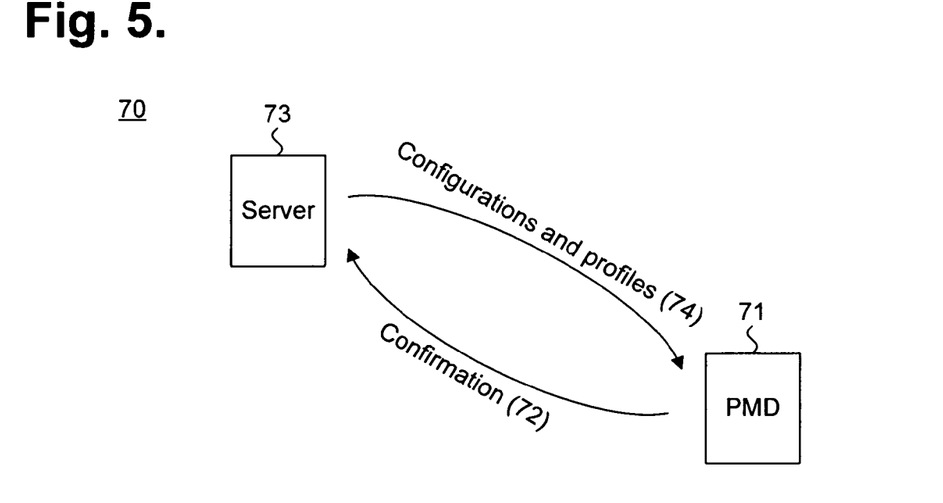
FIG. 5 is a process flow diagram showing server connectivity confirmation in the remote patient care environment of FIG. 1.

During setup, the patient management device-to-centralized server connection is first established. FIG. 5 is a process flow diagram showing server connectivity confirmation 70 in the remote patient care environment 10 of FIG. 1. The initial server connection ensures that the patient management device 12 is properly connected over the applicable connection medium and has the most recent updates of operational parameters and code.

Prior to initial power up, the patient or attendant physically connects the patient management device 71 to the appropriate physical medium, that is, a telephone line or network connection. Thereafter, on initial power up or when requested by the patient 14 or other source, the patient management device 71 attempts to send a confirmation message 72 to an assigned centralized server 73. Upon receiving the confirmation message 72, the centralized server 73 confirms that the requesting patient management device 71 is authorized for access and, if valid, sends a message in reply that contains the most up-to-date configurations and profiles 74 for both the patient management device 71 and those medical devices 15-18 that the centralized server 73 expects to interface. Following successful receipt of the configurations and profiles message 74, the server connection is fully established. Other server connection-related operations are possible.

Medical device setup includes discovery, data exchange, and optional reconfiguration. FIG. 6 is a process flow diagram showing device registration 80 in the remote patient care environment 10 of FIG. 1. In one embodiment, one or more of the medical devices 15-18 interface with patient management devices using the Bluetooth wireless communication protocol. When a medical device needs to communicate with a patient management device, a connection is established using Bluetooth baseband procedures. Once a connection has been established, a Bluetooth communication session begins. Under this protocol, a master-slave model is used under which the medical device 81 functions as a master and each patient management device within range functions as a slave. Consequently, each patient management device must passively wait for a medical device to initiate a connection for patient data upload and medical device reconfiguration.

Initially, the patient management device remains in a powered down or standby state until patient data 88 is available for upload from one of the medical devices. Each patient management device 71, 83, 84 is maintained in a discoverable mode under which the patient management device will respond to discovery requests. The uploading medical device 81 accesses an internal device list 82 to determine the Bluetooth address for the patient management device to which the medical device 81 last successfully connected and performed data upload. If no Bluetooth address can be found, the medical device 81 performs discovery by transmitting a discover request 85*a-c* to those patient medical devices 71, 83, 84 within range. Upon receiving the discovery request 85*a-c*, each receiving patient management device 71, 83, 84 replies with a class of service (COD) message 86*a-c* that identifies the class of service to which the patient management device belongs. The medical device 81 will only connect to those patient management devices belonging to the correct class of device. The Bluetooth addresses 87*a-b* of those COD-matching patient management devices are stored into the device list 82. The functions of master and slave can be interchanged between the medical devices and patient management devices and other forms of device discovery could be used to register devices.

Figure 7:
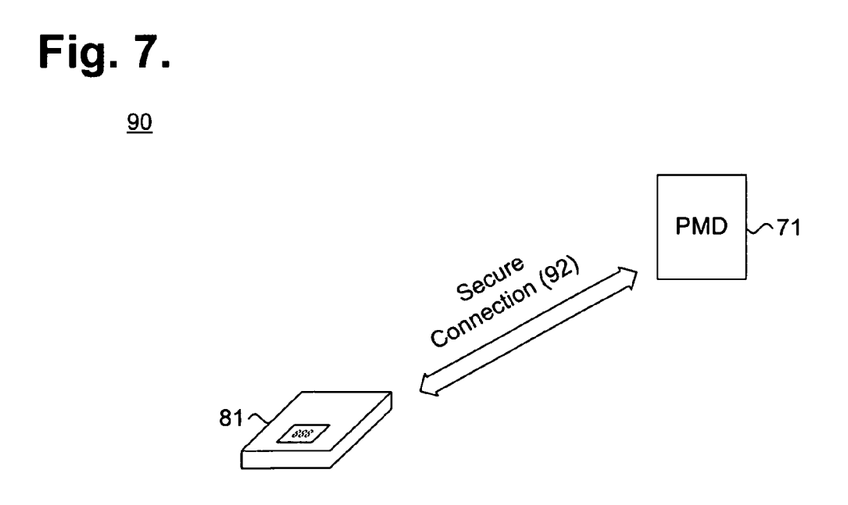
FIG. 7 is a process flow diagram showing patient management device and server connection in the remote patient care environment of FIG. 1.

Patient management device-to-medical device connection occurs upon the initiative of a medical device that is ready to upload patient data. FIG. 7 is a process flow diagram showing patient management device and server connection 90 in the remote patient care environment 10 of FIG. 1. A secure connection 92 is established between the patient medical device 81 and at most one patient management device 71 belonging to the same class of device.

Connection security is provided in three parts. Authentication is provided through standard Bluetooth link layer security, which uses a combination of a personal identification number (PIN), the 24-bit class of device, and, optionally, a service name to generate a unique link key. An integrity seal is provided by the receiving application, either on the patient management device or centralized server 13, which ensures that the received patient data falls within expected bounds. Finally, encryption is provided through standard Bluetooth link layer security, which employs a 128-bit encryption key. Other forms of data security are possible.

Figure 8:
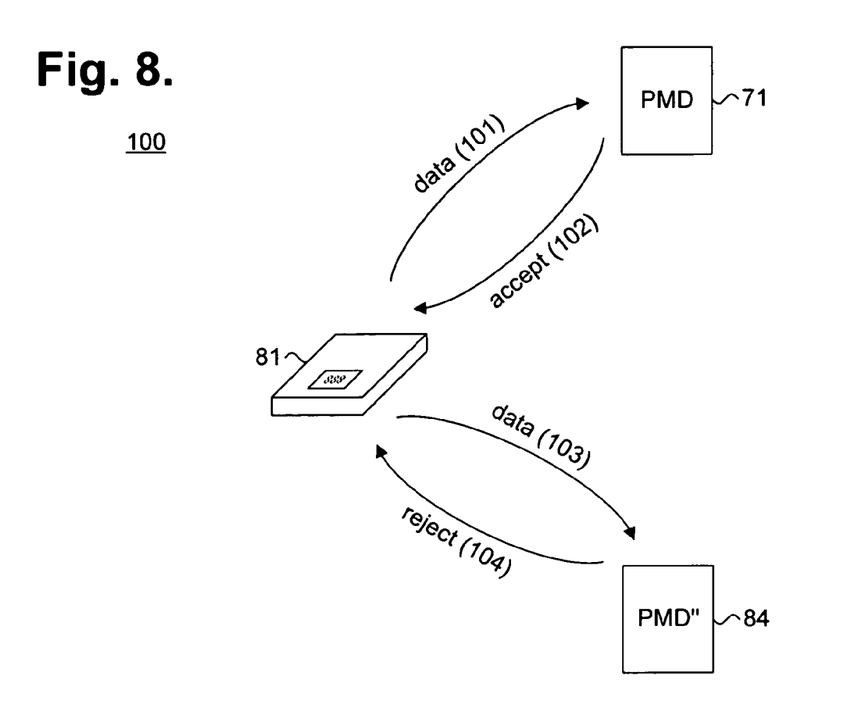
FIG. 8 is a process flow diagram showing data transmission in the remote patient care environment of FIG. 1.

Patient data is conditionally sent from the medical device to the patient management device. FIG. 8 is a process flow diagram showing data transmission 100 in the remote patient care environment 10 of FIG. 1. Each upload of patient data is sent in two parts, which include a header packet followed by a data packet. The data packet is specific to the sending medical device 81 and type of patient data.

The medical device 81 sends the patient data 101 to the securely connected patient management device 71. If only patient data receipt and not reconfiguration is to be performed, the patient medical device 71 replies with an acceptance message 102, which acknowledges receipt of the patient data 101 and enables the medical device 81 to erase the patient data from memory. However, if patient data 103 is sent to a patient management device 84 for which permission for access is not allowed, the patient medical 84 sends a rejection message 104, which signifies that the patient management device 84 has refused the patient data. Each patient management device receives medical device configuration information, including model and serial numbers, type, Bluetooth address, and, optionally, a proprietary personal identification number. Additionally, a service name can be used. The medical device configuration information is used by each patient management device to determine whether patient data received for upload will be accepted or rejected. Other forms of patient data upload acceptance and rejection are possible.

As a patient management device must passively wait for each medical device to attempt patient data upload, the only opportunity for reconfiguration occurs as part of the patient data upload session. FIG. 9 is a process flow diagram showing data transmission and device reconfiguration 110 in the remote patient care environment 10 of FIG. 1. Assuming that a patient management device 71 agrees to accept a patient data upload, the patient management device 71 replies with an acceptance and configuration mode message 111. The medical device 81 replies with a configuration request message 112 that indicates that the medical device 81 has entered into a configurable mode of operation. The patient management device 71 then sends operational parameters 113, which can include both device settings or code that is automatically applied or installed by the medical device 81. Upon attempting reconfiguration, the medical device 81 sends a configuration acknowledgement message 114 that indicates success or failure. Other forms of medical device reconfiguration are possible.

Patient Management Device

Figure 10:
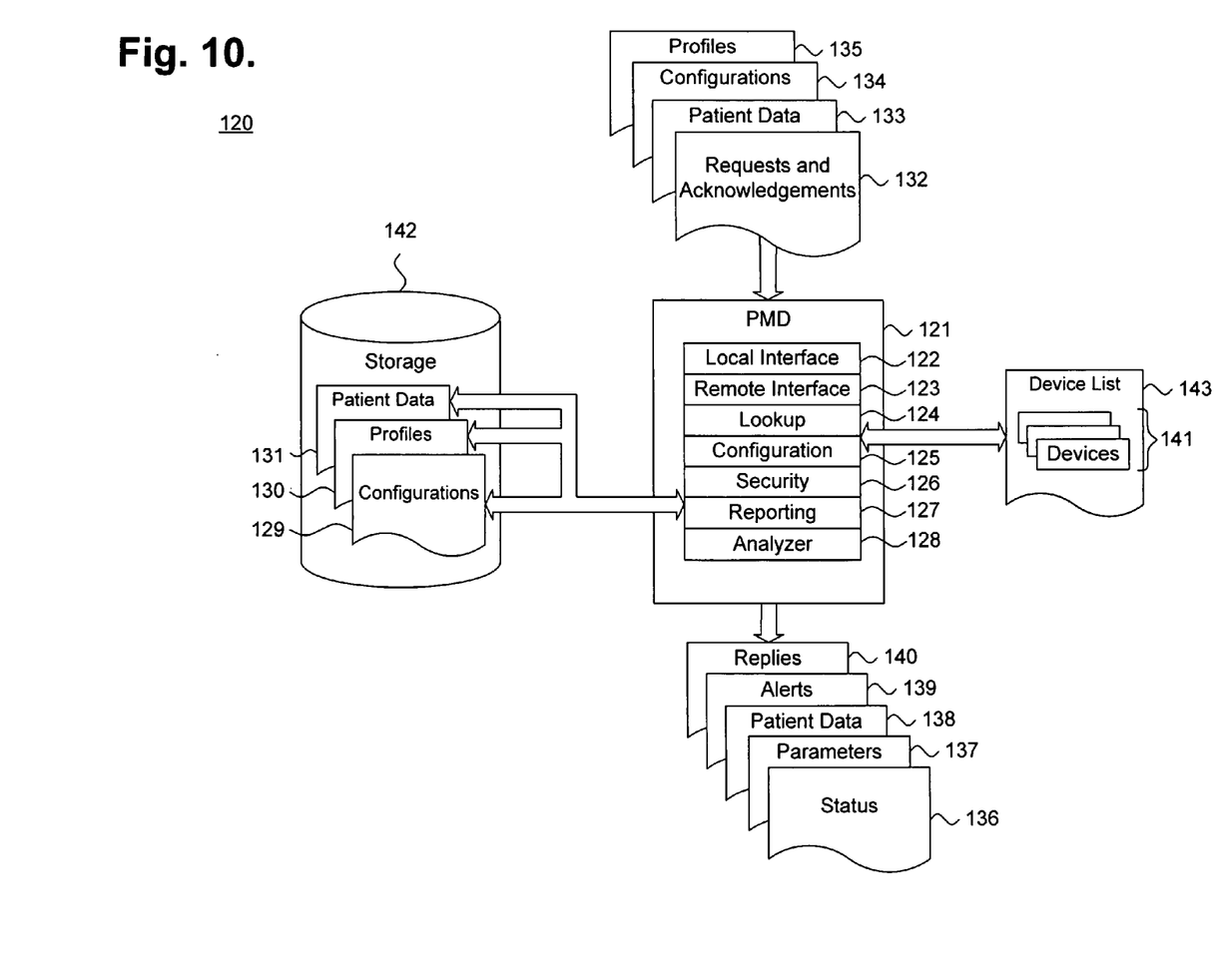
FIG. 10 is a functional block diagram showing a patient management device for use in the remote patient care environment of FIG. 1.

Each patient management device serves as the focal point for forwarding collected patient data to the centralized server and for reconfiguring the medical devices and the patient management device itself. FIG. 10 is a functional block diagram showing a patient management device 121 for use in the remote patient care environment 10 of FIG. 1. In one embodiment, the patient management device 121 executes a sequence of program or process steps, such as described above beginning with reference to FIG. 3, implemented, for instance, on a programmed digital computer or micro-programmable device.

Each patient management device 121 includes a storage device 142 and can be configured to store medical device configurations 129, patient profiles 130, and patient data 131. Other types of stored data are possible. Each patient management device 121 also includes a local interface 122, remote interface 123, lookup module 124, configuration module 125, security module 126, reporting module 127, and, in a further embodiment, an analyzer 128. The local interface 122 provides an external interface by which medical devices 15-18 can connect and perform secure communication sessions using, for example, the Bluetooth wireless communication protocol. Similarly, the remote interface 123 provides an external interface by which the patient management device 121 can securely connect to the centralized server 13 using, for example, a network- or telephone-based communications medium. The lookup module 124 accesses a set of devices with permissions for access 141 maintained in a device list 143 and configurations 129 and patient profiles 130 maintained in the storage device 142 in response to an attempted upload of patient data 133. Authorized medical devices having the correct COD and patient-specific credentials is registered into the device list 143 as a device 141 with permission for access. The lookup module 124 also sends reply messages 140 to data reporting medical devices 15-18, such as class of device, patient data acceptance, patient data rejection, and patient data acceptance and configuration mode.

The configuration module 125 controls the initial and subsequent configuration of the patient management device 121 and reconfiguration of the medical devices 15-18. Upon initial power up or when requested by the patient 14 or other source, the configuration module 125 receives device configurations 134 and patient profiles 135 from the centralized server, which are stored into the storage device 142. The configuration module 125 then induces data reporting by one or more of the medical devices 15-18 through control provided through a user interface 23. For example, the patient 14 could be instructed to perform physical actions that trigger data reporting. Upon receiving the induced data reports, the configuration module 128 performs any configuration required of the patient management device 121 or reconfiguration of the medical devices 15-18 by sending the appropriate parameters and code 137. The security module 126 performs the three-part protection of patient data 133 received from authorized medical devices 15-18 and further performs data protection for the patient data 138 being forwarded to the centralized server 13. The reporting module 127 performs the actual reporting of device status 136 and patient data 138 to the centralized server 13. Device status 136 can include a list of those devices 141, which have been granted permission for access. In a further embodiment, the analyzer 128 locally evaluates uploaded patient data 133 and, as appropriate, generates alerts 139, which are provided to the centralized server 13 and, if appropriate, other recipients, such as the patient via the user interface 23. An alert 139 might be generated locally to the patient if, for instance, connectivity to the centralized server 13 cannot be confirmed. Other forms of patient management device functionality are possible.

While the invention has been particularly shown and described as referenced to the embodiments thereof, those skilled in the art will understand that the foregoing and other changes in form and detail may be made therein without departing from the spirit and scope of the invention.

What is claimed is:

1. A system for providing automatic setup of a remote patient care environment, comprising:
   a first remote interface to confirm connectivity over a network connection to a centralized server; a configuration module on a patient management device to induce data reporting to the patient management device for a patient by wirelessly connectable monitoring devices through control provided through a user interface,
     wherein the induced data reporting establishes an initial connection between each of the monitoring devices and the patient management device,
     wherein the induced data reporting causes the configuration module to execute an automated setup procedure enabling the initial connection and subsequent connections between each of the monitoring devices and the patient management device;
   a lookup module configured to:
     register each of the monitoring devices on a list of devices having permission for access as each monitoring device attempts to establish the initial wireless connection and report the data conditioned on permission for access; and
     look up each of the monitoring devices on the list of devices having permission for access as each monitoring device attempts to establish subsequent wireless connections and report the data conditioned on permission for access; and
   a second remote interface to wirelessly connect with each of the monitoring devices upon granting of the permission for access and to subsequently receive the data over the initial wireless connection; and wherein one or more of the monitoring devices are reconfigured by specifying operational parameters to the device.

2. A system according to claim 1, wherein the operational parameters are selected from the group comprising personal identification number, service name, and time clock.

3. A system according to claim 1, wherein the operational parameters are specified through at least one of the user interface and the centralized server.

4. A system according to claim 1, wherein the registration of each monitoring device is restricted by class.

5. A system according to claim 1, further comprising: a reporting module to generate an alert when the connectivity to the centralized server cannot be confirmed.

6. A system according to claim 1, wherein the remote interface confirms connectivity to the centralized server through access validation, wherein access validation is selected from the group comprising personal identification number, service name, model number, serial number, and device type.

7. A system according to claim 1, wherein at least one of patient profiles and monitoring device configurations are retrieved from the centralized server over the network connection.

8. A system according to claim 1, further comprising: a reporting module to provide a status to the centralized server of each monitoring device that has been granted the permission for access.

9. A system according to claim 1, further comprising: a security module to protect the data received over the wireless connection.

10. A system according to claim 9, wherein the data protection comprises one or more of:
an authentication submodule to authenticate the data upon receipt as to originating source against those monitoring devices to which permission for access has previously been granted;
an integrity submodule to determine integrity of the data upon receipt by evaluating the data against predetermined limits and thresholds; and
an encryption submodule to encrypt the data while in transit over the wireless connection.

11. A system according to claim 1, wherein at least one of the monitoring devices to which permission for access has previously been granted is wirelessly reconnected and further data is subsequently received over the wireless connection.

12. A system according to claim 11, wherein the further data has been temporarily stored due to an unsuccessful wireless reconnection attempt.

13. A system according to claim 1, wherein the wireless connection is implemented as a Bluetooth connection.

14. A system according to claim 1, wherein the monitoring devices comprise an implantable medical device.

15. A system according to claim 1, wherein the one or more monitoring devices comprise one or more external medical devices selected from the group comprising external devices that operate autonomously; external devices that operate under patient, attendant, or caregiver control; and external devices that include a user interface for receiving or providing subjective feedback or communications.

16. A method for providing automatic setup of a remote patient care environment, comprising:
confirming connectivity over a network connection to a centralized server;
inducing data reporting to a patient management device for a patient by wirelessly connectable monitoring devices through control provided through a user interface,
wherein inducing data reporting establishes an initial connection between each of the monitoring devices and the patient management device and causes an automated setup procedure for enabling the initial connection and subsequent connections between each of the monitoring devices and the patient management device;
registering each of the monitoring devices on a list of devices having permission for access as each of the monitoring devices attempts to establish a-wireless-the initial connection and report the data conditioned on permission for access;
looking up each of the monitoring devices on the list of devices having permission for access as each monitoring device attempts to establish subsequent wireless connections and report the data conditioned on permission for access; and
wirelessly connecting with the monitoring device upon granting of the permission for access and subsequently receiving the data over the wireless connection; and
reconfiguring one or more of the monitoring devices by specifying operational parameters to the device.

17. A method according to claim 16, wherein the operational parameters are selected from the group comprising personal identification number, service name, and time clock.

18. A method according to claim 16, wherein the operational parameters are specified through at least one of the user interface and the centralized server.

19. A method according to claim 16, further comprising: restricting the registration of each device by class.

20. A method according to claim 16, further comprising: generating an alert when the connectivity to the centralized server cannot be confirmed.

21. A method according to claim 16, wherein confirming connectivity to a centralized server comprises access validation, wherein access validation is selected from the group comprising personal identification number, service name, model number, serial number, and device type.

22. A method according to claim 16, further comprising: retrieving at least one of patient profiles and device configurations from the centralized server over the network connection.

23. A method according to claim 16, further comprising: providing a status to the centralized server of each device that has been granted the permission for access.

24. A method according to claim 16, further comprising: protecting the data received over the wireless connection.

25. A method according to claim 24, wherein the data protection comprises one or more of: authenticating the data upon receipt as to originating source against those monitoring devices to which permission for access has previously been granted; determining integrity of the data upon receipt by evaluating the data against predetermined limits and thresholds; and encrypting the data while in transit over the wireless connection.

26. A method according to claim 16, further comprising: wirelessly reconnecting with at least one of the monitoring devices to which permission for access has previously been granted and subsequently receiving further data over the wireless connection.

27. A method according to claim 26, wherein the further data has been temporarily stored due to an unsuccessful wireless reconnection attempt.

28. A method according to claim 16, wherein the wireless connection is implemented as a Bluetooth connection.

29. A method according to claim 16, wherein the monitoring devices comprise an implantable medical device.

30. A method according to claim 29, wherein the one or more monitoring devices comprise one or more external medical devices selected from the group comprising external devices that operate autonomously; external devices that operate under patient, attendant, or caregiver control; and external devices that include a user interface for receiving or providing subjective feedback or communications.

31. A non-transitory computer-readable storage medium holding code for performing the steps of:
   confirming connectivity over a network connection to a centralized server;
   inducing data reporting directly to a patient management device for a patient by wirelessly connectable monitoring devices through control provided through a user interface,
   wherein inducing data reporting establishes an initial connection between each of the monitoring automated setup procedure for enabling the initial connection and subsequent connections between each of the monitoring devices and the patient management device;
   registering each of the monitoring devices on a list of devices having permission for conditioned on permission for access;
   looking up each of the monitoring devices on the list of devices having permission for access as each monitoring device attempts to establish subsequent wireless connections and report the data conditioned on permission for access; and
   wirelessly connecting with each monitoring device upon granting of the permission for access and subsequently receiving the data over the wireless connection; and
   reconfiguring one or more of the monitoring devices by specifying operational parameters to the device.

\* \* \* \* \*